(12) United States Patent
Kim et al.

(10) Patent No.: US 8,586,700 B2
(45) Date of Patent: *Nov. 19, 2013

(54) METHOD FOR PREPARING A POLY(ETHER SULFONIMIDE OR -AMIDE) COPOLYMER USING CYCLIC OLIGOMERS

(75) Inventors: Yong Seok Kim, Daejeon (KR); Hyun Min Jung, Daejeon (KR); Jong Chan Won, Daejeon (KR); Jae Heung Lee, Daejeon (KR)

(73) Assignee: Korea Reasearch Institute of Chemical Technology, Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/641,585

(22) PCT Filed: Oct. 7, 2010

(86) PCT No.: PCT/KR2010/006838
§ 371 (c)(1),
(2), (4) Date: Nov. 15, 2012

(87) PCT Pub. No.: WO2011/129501
PCT Pub. Date: Oct. 20, 2011

(65) Prior Publication Data
US 2013/0053530 A1 Feb. 28, 2013

(30) Foreign Application Priority Data

Apr. 16, 2010 (KR) .................. 10-2010-0035530
Apr. 23, 2010 (KR) .................. 10-2010-0038138

(51) Int. Cl.
*C08G 63/02* (2006.01)
(52) U.S. Cl.
USPC ........... 528/271; 528/173; 528/244; 528/360; 528/361
(58) Field of Classification Search
USPC .................. 528/173, 244, 271, 361
See application file for complete search history.

(56) References Cited

U.S. PATENT DOCUMENTS

| 5,071,941 A | 12/1991 | Lubowitz et al. |
| 6,066,710 A | 5/2000 | Becker et al. |
| 2001/0018157 A1 | 8/2001 | Aoki et al. |
| 2006/0292476 A1 | 12/2006 | Maehata et al. |

FOREIGN PATENT DOCUMENTS

JP 2007-292946 A 11/2007

OTHER PUBLICATIONS

Brunelle, Daniel J., et al.: "Semicrystalline Polymers via Ring-Opening Polymerization: Preparation and Polymerization of Alkylene Phthalate Cyclic Oligomers", *Macromolecules*, 1988, 31, pp. 4782-4790.
Wang, Yi-Feng, et al.: "Novel macrocyclic aryl ether oligomers containing a diphenylacetylene moiety: synthesis, characterization and ring-opening polymerization", *Polymer*, vol. 38, No. 2, 1997, pp. 469-482.
Hall, Andrew J., et al.: "Recent research on the synthesis and applications of cyclic oligomers", *Reactive & Functional Polymers*, 41 (1999), pp. 133-139.
Jiang, Hongyan, et al.:"Synthesis and polymerization of some macrocyclic (arylene ether sulfone) containing cardo groups and macrocyclic (Arlene ether ketone sulfone)oligomers", *Polymer*, vol. 39, No. 24, 1998, pp. 6079-6083.
Kim, Young H., et al.: "$CaCl_3$ or $Ca_2Cl_4$ Complexing Cyclic Aromatic Amide. Template Effect on Cyclization", *Journal of American Chemical Society*, 1996, 118, p. 1545-1546.
Wang, Yi-Feng, et al.: "Novel aromatic macrocyclic oligomers: intermediates for the preparation of high-performance polymers", *Reactive & Functional Polymers*, 30 (1996), pp. 205-227.

*Primary Examiner* — Terressa Boykin
(74) *Attorney, Agent, or Firm* — Frommer Lawrence & Haug LLP; Ronald R. Santucci (57) ABSTRACT

Disclosed is a method for preparing a poly(ethersulfonimide or ethersulfonamide) copolymer using cyclic oligomers, and more particularly, to a method for preparing a poly(ethersulfonimide or ethersulfonamide) copolymer by preparing a cyclic ether sulfone oligomer and a cyclic imide or amide oligomer and subjecting the cyclic ether sulfone oligomer and the cyclic imide or amide oligomer to ring-opening copolymerization in the presence of an alkali metal fluoride catalyst.

10 Claims, 3 Drawing Sheets

METHOD FOR PREPARING A POLY(ETHER SULFONIMIDE OR -AMIDE) COPOLYMER USING CYCLIC OLIGOMERS

This application is a 371 of PCT/KR2010/006838 filed on Oct. 7, 2010 published on Oct. 20, 2011 under publication number WO 2011/129501 A which claims priority benefits to Korean Patent Application Number 10-2010-0035530 filed Apr. 16, 2010 and Korean Patent Application Number 10-2010-0038138 filed Apr. 23, 2010, the entire disclosures of which are incorporated herein by reference.

TECHNICAL FIELD

The present invention relates to a method for preparing a poly(ethersulfonimide or ethersulfonamide) copolymer by ring-opening polymerization of an ether sulfone compound and an imide or amide compound in the form of cyclic oligomers.

BACKGROUND ART

Since a process of condensing polyimide and one for condensing a polyethersulfone resin from individual monomers cannot proceed together because of they require different reaction conditions, it is impossible to obtain a copolymer from direct condensation of a diamine compound and an acid dianhydride compound, which are monomers of polyimide, and a dihalogen compound and a diol compound, which are monomers of polyethersulfone. As the existing method of preparing a poly(ethersulfonimide) resin, a method of forming an imide group by cyclodehydration of tetracarboxylic dianhydride with a diamine compound having an ether sulfone moiety is known.

Basically, preparation of a poly(ethersulfonimide) resin by condensation polymerization follows a process of preparing polyimide. Since the ether sulfone moiety is included in the diamine functional group, control of copolymerization ratio is impossible and the polymer length is limited by the diamine compound used as monomer.

Meanwhile, since a process of condensing polyimide and one for condensing a polyethersulfone resin from individual monomers cannot proceed together because of they require different reaction conditions, it is impossible to obtain a copolymer from direct condensation of a diamine compound and a dicarboxylic acid compound or a diacyl halide compound, which are monomers of polyamide, and a dihalogen compound and a diol compound, which are monomers of polyethersulfone. As the existing method of preparing a poly(ethersulfonamide) resin, a method of condensing a diamine compound with a dicarboxylic acid compound or a diacyl chloride compound having an ether sulfone moiety or a method of condensing a dicarboxylic acid compound or a diacyl chloride compound with a diamine compound having an ether sulfone moiety is known.

Basically, preparation of a poly(ethersulfonamide) resin by condensation polymerization follows a process of preparing polyamide. Since the ether sulfone moiety is included in the diamine, dicarboxylic acid or diacyl chloride functional group, control of copolymerization ratio is impossible and the polymer length is limited by the diamine, dicarboxylic acid or diacyl chloride compound used as monomer.

As a method of copolymerizing the poly(ethersulfonimide or ethersulfonamide) resin allowing control of the composition of the ether sulfone moiety and the imide or amide moiety as desired and control of the polymer length through control of the amount of each component, ring-opening polymerization using cyclic oligomers as precursor may be considered. Ring-opening polymerization of polyester, polyetherketone and polyamide resins, wherein the polymerization occurs as cyclic oligomers are ring-opened in the presence of a catalyst, has been disclosed. However, copolymerization of a cyclic imide or amide with a cyclic ether sulfone has not been reported yet. Also, a method of easily controlling the copolymerization ratio by controlling the amount of the two components when preparing a copolymer of imide or amide and ether sulfone is not known yet.

DISCLOSURE

Technical Problem

The inventors of the present invention have developed a method of synthesizing ether sulfone and cyclic imide or amide oligomers and preparing a poly(ethersulfonimide or ethersulfonamide) copolymer by ring-opening polymerization of the cyclic oligomers.

The present invention is directed to providing a method for preparing a poly(ethersulfonimide or ethersulfonamide) copolymer by synthesizing a cyclic ether sulfone oligomer and a cyclic imide or amide oligomer and performing ring-opening polymerization thereof, which allows control of the ratio of the two components as desired without reaction byproducts.

The present invention is also directed to providing a cyclic ether sulfone compound and a cyclic imide or amide compound which are used to prepare the poly(ethersulfonimide or ethersulfonamide) copolymer.

Technical Solution

In an aspect, the present invention provides cyclic oligomers represented by Chemical Formulas 1-3, as monomers for ring-opening polymerization, and a method of ring-opening copolymerizing the cyclic oligomer represented by Formula 1 with the cyclic oligomer represented by Formula 2 or 3 in the presence of a catalyst.

[Formula 1]

In Formula 1, $R_1$ is selected from and $R_2$ and $R_3$, which are the same or different, are selected from and n is an integer from 2 to 10.

[Formula 2]

In Formula 2, $R_1$ is selected from

$R_2$ and $R_3$, which are the same or different, are selected from and n is an integer from 2 to 10.

[Formula 3]

In Formula 3, $R_1$ is selected from $R_2$ and $R_3$, which are the same or different, are selected from and n is an integer from 2 to 10.

In another aspect, the present invention provides a method for preparing a poly(ethersulfonimide) copolymer, comprising ring-opening polymerizing the cyclic oligomers represented by Chemical Formulas 1 and 2 in the presence of a catalyst.

In another aspect, the present invention provides a method for preparing a poly(ethersulfonamide) copolymer, comprising ring-opening polymerizing the cyclic oligomers represented by Chemical Formulas 1 and 3 in the presence of a catalyst.

Advantageous Effects

The preparation method according to the present invention proceeds via a one-pot process. Copolymerization ratio and polymer composition can be controlled easily by controlling the kind and amount of respective cyclic oligomers and reaction byproducts are not formed.

The cyclic ether sulfone oligomer and the cyclic imide or amide oligomer according to the present invention are compounds having 2-10 monomer repeat units. As polymerization proceeds, a copolymer in which blocks of monomer repeat units comprising the ether sulfone and the imide or amide oligomers are formed in the polymer chain is obtained. Since the ether group included in each cyclic oligomer acts as the ring-opening site during the ring-opening polymerization, the polymerization can proceed under relatively mild conditions without affecting the imide or amide and the ether sulfone groups.

BEST MODE FOR CARRYING OUT INVENTION

The cyclic ether sulfone compound represented by Formula 1, the cyclic imide compound represented by Formula 2 and the cyclic amide compound represented by Formula 3 provided by the present invention are prepared under a low-concentration condition by slowly adding the monomer component. The cyclic compound can be selectively prepared by removing the polymers linearly extended and thus having increased molecular weight based on solubility difference. The produced cyclic ether sulfone compound and cyclic imide or amide compound are identified as oligomers consisting of 2-10 monomer units through MALDI-TOF mass spectrometry.

In the method for preparing the cyclic ether sulfone compound according to an embodiment of the present invention, an aliphatic or aromatic dialcohol compound and an aliphatic or aromatic dihalide compound are used as starting materials to prepare the cyclic ether sulfone compound. The cyclic ether sulfone compound contains an ether (—C—O—C—) group at which ring-opening reaction can occur during condensation copolymerization. Reaction is performed in a temperature range from room temperature to 180° C. while slowly adding dropwise the two components at a molar ratio of 1:1 to a reaction solvent. During the reaction, the two components diluted respectively in solvents are slowly added using a feed pump to a reactor in which the reaction solvent is contained. The time until the whole components are added needs to be at least 2 hours such that the concentration of unreacted components in the reactor is not increased. When considering reaction efficiency, the components may be added dropwise for 2-8 hours. To minimize the formation of linear polymers, the amount of the solvent used is determined such that the concentration of the reactants is not greater than 0.1 M. Specifically, the concentration of the reactants is maintained at 0.005-0.1 M. If the concentration of the reactants is 0.1 M or higher, linear polymers may be produced. And, if the concentration of the reactants is 0.005 M or lower, reaction efficiency is decreased. More specifically, the concentration of the reactants may be 0.05-0.01 M. The aromatic or aliphatic dialcohol used in the reaction may be one commonly used in the art and is not particularly limited. Specifically, bissulfonyldiphenol, bisphenol A, bisoxyphenol, bis(diperfluoropropane)diphenol, hydroquinone, resorcinol, naphthalene-2,6-diol, naphthalene-1,7-diol, naphthalene-2,7-diol, biphenyl-4,4-diol, biphenyl-3,4-diol, a fluoro-substituted derivative or an alkyl-substituted derivative may be used alone or in combination. The dihalide may be an aromatic or aliphatic dihalide. Specifically, 4,4'-dichlorophenylsulfone, 4,4'-difluorodiphenylsulfone, 4,4'-dibromodiphenylsulfone, a fluoro-substituted derivative or an alkyl-substituted derivative may be used alone or in combination. The reaction of the dialcohol with the dihalide is carried out in a solvent capable of dissolving these reactants and the prepared compounds. The solvent may be one commonly used in the art and is not particularly limited. Specifically, N,N-dimethylformamide, N,N-dimethylacetamide, N-methyl-2-pyrrolidone, cresol, pyridine, dimethyl sulfoxide, □-butyrolactone, etc. and a mixture thereof may be used.

In the method for preparing the cyclic imide compound according to another embodiment of the present invention, a cyclic amic acid compound used as a precursor may be prepared using monomers commonly used for preparation of polyimide. That is to say, an aliphatic or aromatic tetracarboxylic dianhydride and an aliphatic or aromatic diamine are used as starting materials. For the diamine monomer, one having an ether (—C—O—C—) group at which ring-opening reaction can occur during copolymerization is used. Reaction is performed in a temperature range from −20° C. to room temperature while slowly adding dropwise the two components at a molar ratio of 1:1 to a reaction solvent. During the reaction, the two components diluted respectively in solvents are slowly added using a feed pump to a reactor in which the reaction solvent is contained. The time until the whole components are added needs to be at least 2 hours such that the concentration of unreacted components in the reactor is not increased. When considering reaction efficiency, the components may be added dropwise for 2-8 hours. To minimize the formation of linear polymers, the amount of the solvent used is determined such that the concentration of the reactants is not greater than 0.1 M. Specifically, the concentration of the reactants is maintained at 0.005-0.1 M. If the concentration of the reactants is 0.1 M or higher, linear polymers may be produced. And, if the concentration of the reactants is 0.005 M or lower, reaction efficiency is decreased. More specifically, the concentration of the reactants may be 0.05-0.01 M. The tetracarboxylic dianhydride used in the reaction may be one commonly used in the art and is not particularly limited. Specifically, pyromellitic dianhydride, 1,2,3,4-benzenetetracarboxylic dianhydride, benzophenoetetracarboxylic dianhydride, bis(dicarboxyphenyl)ether dianhydride, bis(dicarboxyphenyl)sulfone dianhydride, bis(dicarboxyphenyl)sulfide dianhydride, bis(dicarboxyphenyl)propane dianhydride, bis(dicarboxyphenyl)hexafluoropropane dianhydride, biphenyltetracarboxylic dianhydride, naphthalenetetracarboxylic dianhydride, a fluoro-substituted derivative or an alkyl-substituted derivative thereof may be used alone or in combination. The acid dianhydride having an aliphatic carbon backbone may be one commonly used in the art. Specifically, cyclobutanetetracarboxylic dianhydride may be used. The diamine may be an aromatic or aliphatic diamine. Specifically, 3,3'-oxydibenzenamine, 3,4'-oxydibenzenamine, 4,4'-oxydibenzenamine,
3,3'-(1,3-phenylenebis(oxy))dibenzenamine,
3,3'-(1,4-phenylenebis(oxy))dibenzenamine,
4,4'-(1,4-phenylenebis(oxy))dibenzenamine,
4,4'-(4,4'-sulfonylbis(1,4-phenylene)bis(oxy))dibenzenamine,
2,2-bis(4-(4-aminophenoxy)phenyl)propane,
2,2-bis(4-(4-aminophenoxy)phenyl)hexafluoropropane, a fluoro-substituted derivative or an alkyl-substituted derivative thereof may be used alone or in combination. The reaction of the acid dianhydride with the diamine is carried out in a solvent capable of dissolving these reactants and the target compound which is amic acid. The solvent may be one commonly used in the art and is not particularly limited. Specifically, N,N-dimethylformamide, N,N-dimethylacetamide, N-methyl-2-pyrrolidone, cresol, pyridine, dimethyl sulfoxide, □-butyrolactone, etc. and a mixture thereof may be used.

After the cyclic amic acid compound is prepared, a cyclic imide compound is prepared therefrom by adding triethylamine and acetic dianhydride and stirring at 50-80° C. for at least 12 hours, whereby the cyclic imide is formed as the imide ring is closed.

The cyclic amide compound prepared and used in the present invention may be prepared according to a general method disclosed in the literature (Y. H. Kim et al, *J. Am. Chem. Soc.* 1996, 118, 1545). Specifically, a diacyl chloride compound and diamine are slowly added dropwise to a solution of triethylamine in N,N-dimethylacetamide. After stirring at room temperature, the produced salt and solvent are removed, and the cyclic amide compound is obtained after drying.

For copolymerization with the cyclic ether sulfone compound, the cyclic amide compound should have an ether group. That is to say, as in the preparation of the cyclic amide compound, the diamine used for ring-opening copolymerization with the cyclic ether sulfone compound has an ether (—C—O—C—) group at which ring-opening reaction can occur during the copolymerization. Specifically, 3,3'-oxydibenzenamine, 3,4'-oxydibenzenamine, 4,4'oxydibenzenamine,
3,3'-(1,3-phenylenebis(oxy))dibenzenamine,
3,3'-(1,4-phenylenebis(oxy))dibenzenamine,
4,4'-(1,4-phenylenebis(oxy))dibenzenamine,
4,4'-(4,4'-sulfonylbis(4,1-phenylene)bis(oxy))dibenzenamine,
2,2-bis(4-(4-aminophenoxy)phenyl)propane,
2,2-bis(4-(4-aminophenoxy)phenyl)hexafluoropropane, a fluoro-substituted derivative or an alkyl-substituted derivative thereof may be used alone or in combination. For the diacyl chloride compound, one derived from an aromatic or aliphatic dicarboxylic acid which is commonly used for preparation of polyamide is used. Specifically, phthaloyl chloride, isophthaloyl chloride, terephthaloyl chloride, naphthyl diacyl chloride, biphenyl diacyl chloride, succinyl chloride, glutaryl dichloride, adipoyl chloride, sebacoyl chloride, etc. may be used.

The diacyl chloride compound and the diamine compound are diluted respectively in solvents and a solution of triethylamine in N,N-dimethylacetamide is slowly added dropwise for 2-10 hours using a syringe pump to form cyclic amide, which is obtained by removing the produced salt and solvent.

The cyclic ether sulfone compound and the cyclic imide or amide compound may be polymerized while controlling copolymerization ratio as desired by controlling the kind and ratio of the two cyclic monomers. The polymerization of the cyclic compounds proceeds as the ether group of each ring is broken and linked. This reaction may be catalyzed an alkali metal fluoride such as LiF, NaF, KF or CsF. Among them, CsF is most suitable because it is fairly soluble in organic solvents and the fluoride ion is easily dissociated. The fluoride ion attacks the ether group to form an oxy anion and phenyl fluoride, which trigger transetherification at the ether group of another ring, thus forming a linear polymer. In particular, the ring-opening polymerization proceeds successfully when there are ether sulfone and imide or amide functional groups. When the cyclic ether sulfone compound is reacted with the cyclic imide or amide compound, a copolymer may be obtained. The prepared poly(ethersulfonimide) copolymer has a molecular weight of 10,000-100,000 g/mol ($M_w$) as determined by GPC and has a copolymerization ratio of from 1:10 to 10:1 (molar ratio) for the ether sulfone repeat unit and the imide repeat unit. And, the prepared poly(ethersulfonamide) copolymer has a molecular weight of 15,000-50,000 g/mol ($M_w$) as determined by GPC and has a copolymerization ratio of from 1:10 to 10:1 (molar ratio) for the ether sulfone repeat unit and the amide repeat unit.

The specific ring-opening copolymerization condition is as follows. The cyclic ether sulfone compound and the cyclic imide or amide compound respectively dissolved in DMSO solvents are reacted by stirring for 2-12 hours at 100-180° C. at normal pressure under nitrogen atmosphere after adding 1-20 mol % of an alkali metal fluoride such as CsF based on the repeat units of the cyclic oligomers. If the reaction temperature is 100° C. or lower, the reaction may not proceed. And, if the reaction temperature is 180° C. or above, the reaction cannot proceed at normal pressure since it exceeds the boiling temperature of the solvent. If the concentration of the alkali metal fluoride is lower than 1 mol %, reaction rate is very low and a large amount of the cyclic oligomers remain unreacted. And, if the concentration of the alkali metal fluoride exceeds 20 mol %, average molecular weight of the polymer decreases. The reaction time needs not be longer than 12 hours since all the cyclic oligomers will have participated in the reaction and been consumed. And, if the reaction time is shorter than 2 hours, a large amount of the cyclic oligomers will remain unreacted.

The ring-opening polymerization begins as the ether group of a cyclic oligomer is opened by the alkali metal fluoride as an alkoxy terminal. A polymer chain grows the ether group of another cyclic oligomer is successively added to the alkoxy terminal. During the polymerization, the cyclic imide or amide oligomer and the cyclic ether sulfone oligomer randomly participate in the reaction, resulting in a copolymer chain. However, the resulting poly(ethersulfonimide or ethersulfonamide) copolymer contains 2-10 paired blocks comprising ether sulfone and imide or amide oligomer repeat units since the ether sulfone and imide or amide oligomers have 2-10 monomer repeat units.

Hereinafter, the present invention will be described in further detail through examples. However, the present invention is not limited by the following examples.

EXAMPLES

Synthesis Example 1

Figure 1:
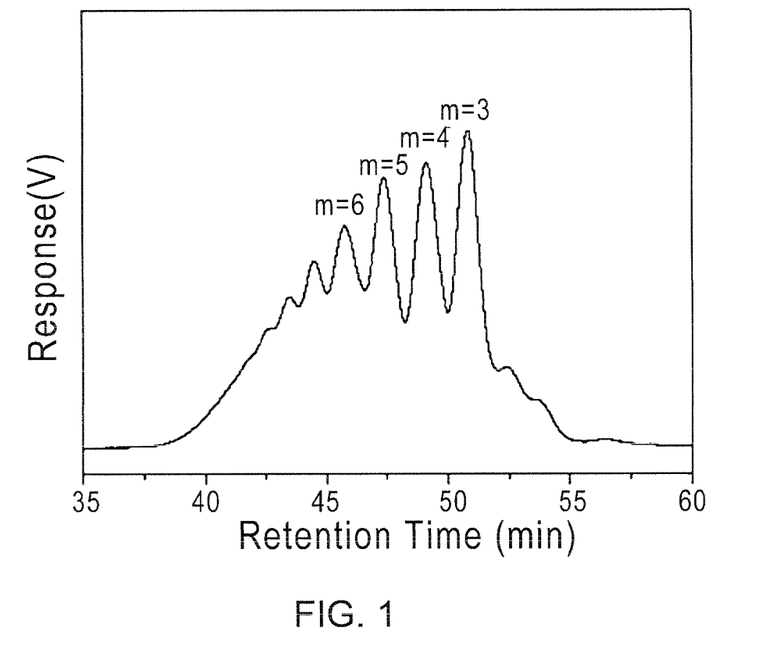
FIG. 1 shows a GPC chromatogram of a cyclic ether sulfone oligomer prepared in Synthesis Example 1.

Synthesis of Cyclic Ether Sulfone Oligomer 560 mL of dimethylacetamide (DMAc), 80 mL of toluene and 1.05 g of $K_2CO_3$ were added to a 1000-mL three-bulb flask equipped with a thermometer, a Dean-Stark trap and a condenser under nitrogen atmosphere and temperature was raised to 150° C. After stirring for 3 hours while removing water and toluene using the Dean-Stark trap, 2.12 g of bisphenol A and 1.67 g of 4,4-dichlorophenylsulfone (DCDPS) respectively dissolved in 20 mL of DMAc were added at a rate of 0.7 mL/hr using a syringe pump. Total reaction time was 72 hours. After the reaction was completed, the reaction solution was filtered to remove the produced salt. The filtrate was concentrated, precipitated by adding cold distilled water, filtered, and then washed with methanol. The filtered product was dissolved in ethyl acetate and filtered to remove undissolved substances. After precipitating by adding methanol, the precipitate was recovered and dried in a vacuum oven at 60° C. for 24 hours. A cyclic ether sulfone oligomer (Formula 1a) in the form of yellowish powder was obtained with a yield of 43.0%. GPC chromatogram of the oligomer is shown in FIG. 1.

$^1$H-NMR (ppm): δ 7.81 (d, 2H, J=8.7 Hz), 7.20 (d, 2H, J=8.8 Hz), 6.98 (d, 2H, J=8.6 h Hz), 6.91 (d, J=8.2 Hz), 1.7 (s, $CH_3$).

FT-IR ($cm^{-1}$): 1488 ($SO_2$).

Mass: 1349 (n=3), 1792 (n=4), 2235 (n=5), 2678 (n=6), 3120 (n=7), 3563 (n=8).

[Formula 1a]

In Formula 1a, each of $R_1$, $R_2$ and $R_3$ is and n is an integer from 3 to 10.

Synthesis Example 2

Figure 2:
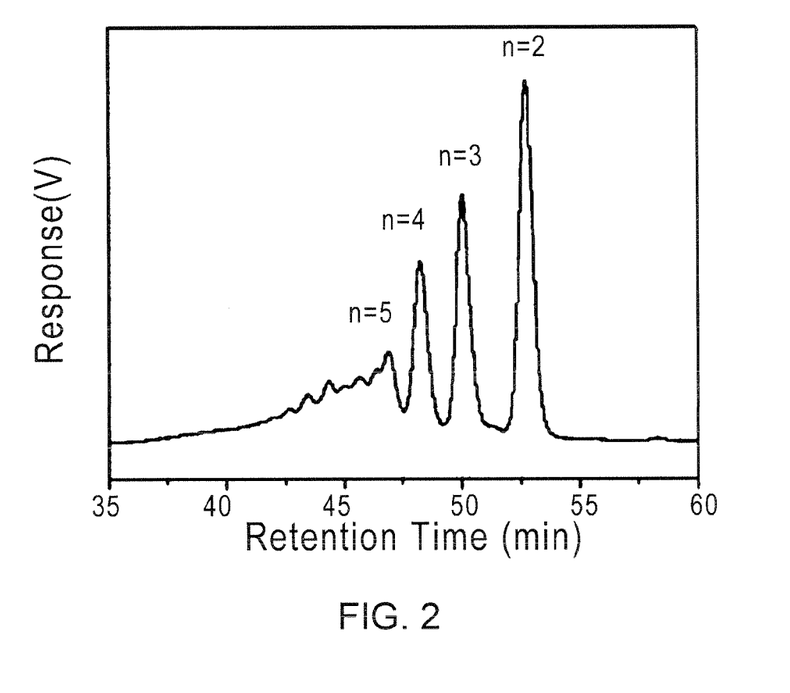
FIG. 2 shows a GPC chromatogram of a cyclic imide oligomer prepared in Synthesis Example 2.

Synthesis Cyclic Imide Oligomer 170 mL of N,N-dimethylformamide (DMF) was added to a five-necked 500-mL round-bottom flask equipped with a mechanic stirrer and a nitrogen inlet under nitrogen flow. After adding 1.78 g (4.0 mmol) of 4,4'-(hexafluoroisopyridine)diphthalic anhydride (6-FDA) and 0.80 g (4.0 mmol) of 3,4-oxydianiline (3,4-ODA), respectively dissolved in 40 mL of DMF, for 8 hours using a syringe pump, the mixture was stirred at room temperature for 8 hours. After adding 5 mL of acetic anhydride and 3 mL of triethylamine, the mixture was stirred at 50° C. for 24 hours. After the reaction was completed, the solvent was removed and the product was dried in a vacuum oven for 2 days. A cyclic imide oligomer (Formula 2a) was obtained with a yield of 59.6%. GPC chromatogram of the oligomer is shown in FIG. 2.

$^1$H-NMR (ppm): δ 8.20-8.28 (d, 2H), 7.92-7.90 (d, 2H), 7.73 (s, 2H), 7.57-7.72 (dd, 8H).

IR ($cm^{-1}$): 1721 (C=O), 1367 (C—N).

Mass (m/z): 1826 (n=3), 2436 (n=4), 3044 (n=5), 3653 (n=6), 4261 (n=7), 4869 (n=8), 5477 (n=9), 6085 (n=10).

[Formula 2a]

In Formula 2, $R_1$ is $R_2$ is

, $R_3$ is

, and n is an integer from 3 to 10.

Synthesis Example 3

Synthesis Cyclic Amide Oligomer

120 mL of DMF was added to a five-necked 500-mL round-bottom flask equipped with a mechanic stirrer and a nitrogen inlet under nitrogen flow. Then, 0.022 g (0.2 mmol) of 1,4-diazabicyclo[2.2.2]octane (DABCO) and 2.1 mL (15 mmol) of triethylamine were injected.

Figure 3:
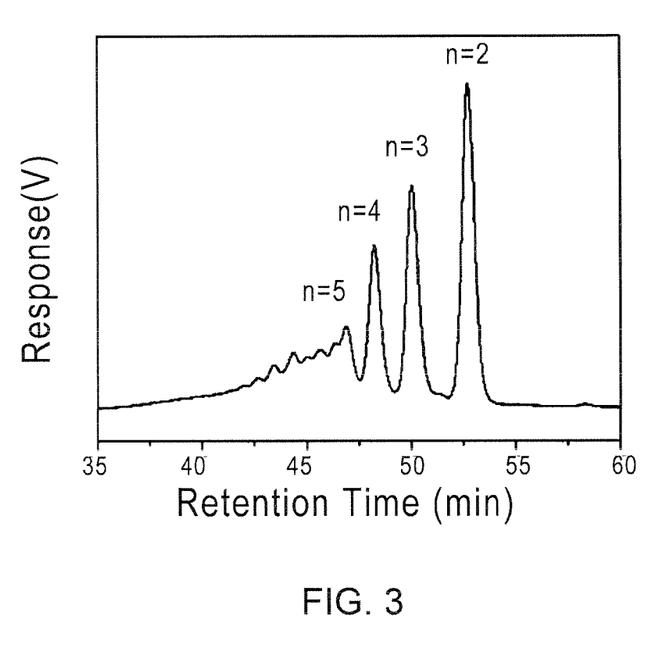
FIG. 3 shows a GPC chromatogram of a cyclic amide oligomer prepared in Synthesis Example 3.

After adding 1.015 g (5 mmol) of isophthaloyl chloride (IPC) and 1.002 g (5 mmol) of 3,4-ODA, respectively dissolved in 40 mL of DMAc, for 8 hours using a syringe pump, the mixture was stirred at room temperature for 24 hours. After the reaction was completed, the produced salt and solvent were removed and the product was dried in a vacuum oven at 80° C.' for 2 days. A cyclic amide oligomer having an amide group (Formula 3a) was obtained with a yield of 64.8%. GPC chromatogram of the oligomer is shown in FIG. 3.

$^1$H-NMR (ppm): δ 10.45 (s, 2H), δ 8.48 (s, 1H), δ 8.07-8.12 (d, 2H), δ 7.73-7.80 (d, 2H), δ 7.65-7.67 (t, 1H), δ 7.52 (s, 2H), δ 7.30-7.36 (t, 1H), δ 7.06-7.09 (d, 2H), δ 6.76-6.97 (d, 1H).

IR (cm$^{-1}$): 1656 (C=O), 1597 (C—N).

Mass (m/z) $(C_n+Li)^+$: 667 (n=2), 997 (n=3), 1328 (n=4), 1658 (n=5), 1983 (n=6).

[Formula 3a]

In Formula 3a, $R_1$ is

, $R_2$ is

, $R_3$ is

, and n is an integer from 3 to 10.

Example 1

0.2 g of the cyclic ether sulfone oligomer synthesized in Synthesis Example 1 and 0.28 g of the cyclic imide oligomer synthesized in Synthesis Example 2 were dissolved at 100° C. under nitrogen flow in 2 mL of dimethyl sulfoxide (DMSO) in a three-necked 50-mL round-bottom flask equipped with a nitrogen inlet and a condenser. After adding 0.015 g of cesium fluoride (CsF), the mixture was stirred at 170° C. for 9 hours. After precipitating by adding distilled water, thus obtained copolymer precipitate was washed with distilled water and then with ethyl acetate and dried in a vacuum oven at 80° C. for 2 days. A poly(ethersulfonimide) copolymer was obtained with a yield of 88%.

$^1$H-NMR (ppm): δ 10.45 (s, 2H), 8.49-6.73 (28H), 1.59 (s, 6H).

IR (neat, cm$^{-1}$): 1721 (C=O), 1367 (C—N), 1488 (SO$_2$).

$M_w$: 23,000, PDI: 1.8.

Example 2

0.29 g of the cyclic ether sulfone oligomer synthesized in Synthesis Example 1 and 0.2 g of the cyclic imide oligomer synthesized in Synthesis Example 2 were dissolved at 100° C. under nitrogen flow in 2 mL of DMSO in a three-necked 50-mL round-bottom flask equipped with a nitrogen inlet and a condenser. After adding 0.015 g of CsF, the mixture was stirred at 170° C. for 9 hours. After precipitating by adding distilled water, thus obtained copolymer precipitate was washed with distilled water and then with ethyl acetate and dried in a vacuum oven at 80° C. for 2 days. A poly(ethersulfonimide) copolymer was obtained with a yield of 85%.

$^1$H-NMR (ppm): δ 10.55 (s, 2H), 8.35-6.68 (44H), 1.56 (s, 12H).

IR (cm$^{-1}$): 1721 (C=O), 1367 (C—N), 1488 (SO$_2$).

$M_w$: 19,500, PDI: 1.6.

Example 3

0.29 g of the cyclic ether sulfone oligomer synthesized in Synthesis Example 1 and 0.1 g of the cyclic imide oligomer synthesized in Synthesis Example 2 were dissolved at 100° C. under nitrogen flow in 2 mL of DMSO in a three-necked 50-mL round-bottom flask equipped with a nitrogen inlet and a condenser. After adding 0.012 g of CsF, the mixture was stirred at 170° C. for 9 hours. After precipitating by adding distilled water, thus obtained copolymer precipitate was washed with distilled water and then with ethyl acetate and dried in a vacuum oven at 80° C. for 2 days. A poly(ethersulfonimide) copolymer was obtained with a yield of 94%.

$^1$H-NMR (ppm): δ 10.46 (s, 2H), 8.45-6.66 (76H), 1.51 (s, 24H).

IR (cm$^{-1}$): 1721 (C=O), 1367 (C—N), 1488 (SO$_2$).

$M_w$: 19,000, PDI: 1.3.

Example 4

0.1 g of the cyclic ether sulfone oligomer synthesized in Synthesis Example 1 and 0.28 g of the cyclic imide oligomer synthesized in Synthesis Example 2 were dissolved at 100° C. under nitrogen flow in 2 mL of DMSO in a three-necked 50-mL round-bottom flask equipped with a nitrogen inlet and a condenser. After adding 0.015 g of CsF, the mixture was stirred at 170° C. for 9 hours. After precipitating by adding distilled water, thus obtained copolymer precipitate was washed with distilled water and then with ethyl acetate and dried in a vacuum oven at 80° C. for 2 days. A poly(ethersulfonimide) copolymer was obtained with a yield of 89%.

$^1$H-NMR (ppm): δ 10.45 (s, 2H), 8.49-6.73 (28H), 1.59 (s, 6H).

IR (neat, cm$^{-1}$): 1721 (C=O), 1367 (C—N), 1488 (SO$_2$).

$M_w$: 28,000, PDI: 1.6.

Comparative Example 0.28 g of a linear imide oligomer (n=3-10) obtained from 6-FDA and 3,4-ODA and 0.20 g of a linear ether sulfone oligomer (n=3-8) obtained from 4,4'-dichlorophenylsulfone and 4,4'-dihydroxydiphenylsulfone were dissolved at 100° C. under nitrogen flow in 2 mL of DMSO in a three-necked 50-mL round-bottom flask equipped with a nitrogen inlet and a condenser. After adding 0.015 g of CsF, the mixture was stirred at 170° C. for 9 hours. After precipitating by adding distilled water, thus obtained copolymer precipitate was washed with distilled water and then with ethyl acetate and dried in a vacuum oven at 80° C. for 2 days. An oligomer mixture was obtained as white solid with a yield of 78%.

$^1$H-NMR (ppm): δ 8.20-8.28 (d, 2H), 7.92-7.90 (d, 2H), 7.73 (s, 2H), 7.57-7.72 (dd, 8H).

IR (cm$^{-1}$): 1721 (C=O), 1367 (C—N).

$M_w$: 5,200.

Copolymerization ratio and molecular weight of the poly(ethersulfonimide) copolymers prepared in Examples 1-4 and Comparative Example 1 are given in Table 1.

TABLE 1

| | Ratio of cyclic ether sulfone/cyclic imide used (molar ratio of repeat units) | Molecular weight of copolymer ($M_w$) | Ratio of ether sulfone/imide in co-polymer (molar ratio of repeat units) |
|---|---|---|---|
| Example 1 | 1:1 | 23,000 | 1:2.1 |
| Example 2 | 2:1 | 19,500 | 1.2:1 |
| Example 3 | 4:1 | 19,000 | 4.6:1 |
| Example 4 | 1:2 | 28,000 | 1:2.5 |
| Comparative Example 1 | 1:1 | 5,200 | — |

As shown in Table 1, the copolymerization ratio of the poly(ethersulfonimide) copolymers according to the present invention, which were polymerized from cyclic oligomers, could be controlled variously by controlling the ratio of the ether sulfone and imide oligomers used.

When the linear oligomers were used instead of the cyclic oligomers (Comparative Example 1), a copolymer having a molecular weight of 10,000 or larger could not be produced by the catalytic reaction. In contrast, high-molecular-weight poly(ethersulfonimide) copolymers could be prepared by the copolymerization according to the present invention.

Example 5

0.27 g of the cyclic ether sulfone oligomer synthesized in Synthesis Example 1 and 0.2 g of the cyclic amide oligomer synthesized in Synthesis Example 3 were dissolved at 100° C. under nitrogen flow in 2 mL of DMSO in a three-necked 50-mL round-bottom flask equipped with a nitrogen inlet and a condenser. After adding 0.014 g of CsF, the mixture was stirred at 170° C. for 9 hours. After precipitating by adding distilled water, thus obtained copolymer precipitate was washed with distilled water and then with ethyl acetate and dried in a vacuum oven at 80° C. for 2 days. A poly(ethersulfonamide) copolymer was obtained with a yield of 82%.

$^1$H-NMR (ppm): δ 8.14 (d, 2H), 7.90-6.96 (28H), 1.57 (s, 6H).

IR (neat, cm$^{-1}$): 1656 (C=O), 1597 (C—N), 1488 (SO$_2$).

$M_w$: 18,000, PDI: 1.64.

Example 6

0.54 g of the cyclic ether sulfone oligomer synthesized in Synthesis Example 1 and 0.2 g of the cyclic amide oligomer synthesized in Synthesis Example 3 were dissolved at 100° C. under nitrogen flow in 2 mL of DMSO in a three-necked 50-mL round-bottom flask equipped with a nitrogen inlet and a condenser. After adding 0.028 g of CsF, the mixture was stirred at 170° C. for 9 hours. After precipitating by adding distilled water, thus obtained copolymer precipitate was washed with distilled water and then with ethyl acetate and dried in a vacuum oven at 80° C. for 2 days. A poly(ethersulfonamide) copolymer was obtained with a yield of 88%.

$^1$H-NMR (ppm): δ 8.19 (d, 2H), 7.91-6.73 (44H), 1.51 (s, 12H).

IR (cm$^{-1}$): 1656 (C=O), 1597 (C—N), 1488 (SO$_2$).

$M_w$: 17,800, PDI: 1.62.

Example 7

0.68 g of the cyclic ether sulfone oligomer synthesized in Synthesis Example 1 and 0.1 g of the cyclic amide oligomer synthesized in Synthesis Example 3 were dissolved at 100° C. under nitrogen flow in 2 mL of DMSO in a three-necked 50-mL round-bottom flask equipped with a nitrogen inlet and a condenser. After adding 0.028 g of CsF, the mixture was stirred at 170° C. for 9 hours. After precipitating by adding distilled water, thus obtained copolymer precipitate was washed with distilled water and then with ethyl acetate and dried in a vacuum oven at 80° C. for 2 days. A poly(ethersulfonamide) copolymer was obtained with a yield of 85%.

$^1$H-NMR (ppm): δ 8.24 (d, 2H), 7.83-6.88 (92H), 1.52 (s, 30H).

IR (cm$^{-1}$): 1656 (C=O), 1597 (C—N), 1488 (SO$_2$).

$M_w$: 15,300, PDI: 1.46.

Comparative Example 2

0.20 g of a linear amide oligomer (n=3-10) obtained from IPC and 3,4-ODA and 0.27 g of a linear ether sulfone oligomer (n=3-8) obtained from 4,4'-dichlorophenylsulfone and 4,4'-dihydroxydiphenylsulfone were dissolved at 100° C. under nitrogen flow in 2 mL of DMSO in a three-necked 50-mL round-bottom flask equipped with a nitrogen inlet and a condenser. After adding 0.015 g of CsF, the mixture was stirred at 170° C. for 9 hours. After precipitating by adding distilled water, thus obtained copolymer precipitate was washed with distilled water and then with ethyl acetate and dried in a vacuum oven at 80° C. for 2 days. An oligomer mixture was obtained as white solid with a yield of 66%.

$^1$H-NMR (ppm): δ 8.14 (d, 2H), 7.90-6.96 (28H), 1.57 (s, 6H).

IR (cm$^{-1}$): 1656 (C=O), 1597 (C—N), 1488 (SO$_2$).

$M_w$: 5,400.

Copolymerization ratio and molecular weight of the poly(ethersulfonamide) copolymers prepared in Examples 5-7 and Comparative Example 2 are given in Table 2.

TABLE 2

| | Ratio of cyclic ether sulfone/cyclic amide used (molar ratio of repeat units) | Molecular weight of copolymer ($M_w$) | Ratio of ether sulfone/amide in copolymer (molar ratio of repeat units) |
|---|---|---|---|
| Example 5 | 1:1 | 18,000 | 1:2.4 |
| Example 6 | 2:1 | 17,800 | 1:1.4 |
| Example 7 | 5:1 | 15,300 | 2.3:1 |
| Comparative Example 2 | 1:1 | 5,400 | — |

As shown in Table 2, the copolymerization ratio of the poly(ethersulfonamide) copolymers according to the present invention, which were polymerized from cyclic oligomers, could be controlled variously by controlling the ratio of the ether sulfone and amide oligomers used.

When the linear oligomers were used instead of the cyclic oligomers (Comparative Example 2), a copolymer having a molecular weight of 10,000 or larger could not be produced by the catalytic reaction. In contrast, high-molecular-weight poly(ethersulfonamide) copolymers could be prepared by the copolymerization according to the present invention.

The invention claimed is:

1. An oligomer for copolymerization of a poly(ethersulfonimide or ethersulfonamide) copolymer, which is a cyclic ether sulfone compound represented by Formula 1:

[Formula 1]

wherein R$_1$ is selected from

R$_2$ and R$_3$, which are the same or different, are selected from and n is an integer from 2 to 10.

2. An oligomer for copolymerization of a poly(ethersulfonimide) copolymer, which is a cyclic imide compound represented by Formula 2:

[Formula 2]

wherein $R_1$ is selected from and $R_2$ and $R_3$, which are the same or different, are selected from and and n is an integer from 2 to 10.

3. An oligomer for copolymerization of a poly(ethersulfonamide) copolymer, which is a cyclic amide compound represented by Formula 3:

[Formula 3]

wherein $R_1$ is selected from and

-continued

$R_2$ and $R_3$, which are the same or different, are selected from and and n is an integer from 2 to 10.

4. A poly(ethersulfonimide) copolymer prepared by polymerizing the oligomer according to claim 1 with the oligomer for copolymerization of a poly(ethersulfonimide) copolymer, which is a cyclic imide compound represented by Formula 2:

[Formula 2]

wherein $R_1$ is selected from

-continued and $R_2$ and $R_3$, which are the same or different, are selected from and n is an integer from 2 to 10.

5. The poly(ethersulfonimide) copolymer according to claim 4, which has a weight-average molecular weight ($M_w$) of 10,000-100,000 g/mol.

6. A poly(ethersulfonamide) copolymer prepared by polymerizing the oligomer according to claim 1 with the oligomer for copolymerization of a poly(ethersulfonamide) copolymer, which is a cyclic amide compound represented by Formula 3:

[Formula 3]

wherein $R_1$ is selected from $R_2$ and $R_3$, which are the same or different, are selected from and n is an integer from 2 to 10.

7. The poly(ethersulfonamide) copolymer according to claim 6, which has a weight-average molecular weight ($M_w$) of 15,000-40,000 g/mol.

8. A method for preparing a poly(ethersulfonimide or ethersulfonamide) copolymer, comprising ring-opening polymerizing a reactant mixture comprising the oligomer according to claim 1 with the oligomer for copolymerization of a poly(ethersulfonimide) copolymer, which is a cyclic imide compound represented by Formula 2:

[Formula 2]

wherein $R_1$ is selected from and n is an integer from 2 to 10 at a molar ratio of from 1:10 to 10:1 in the presence of an alkali metal fluoride catalyst.

9. The method according to claim 8, wherein the alkali metal fluoride catalyst is selected from LiF, NaF, KF and CsF.

10. A method for preparing a poly(ethersulfonimide or ethersulfonamide) copolymer, comprising ring-opening polymerizing a reactant mixture comprising the oligomer according to claim 1 with the oligomer for copolymerization of a poly(ethersulfonamide) copolymer, which is a cyclic amide compound represented by Formula 3:

[Formula 3]

wherein $R_1$ is selected from

$R_2$ and $R_3$, which are the same or different, are selected from $R_2$ and $R_3$, which are the same or different, are selected from -continued and n is an integer from 2 to 10 at a molar ratio of from 1:10 to 10:1 in the presence of an alkali metal fluoride catalyst.

* * * * *